United States Patent [19]

Lundquist

[11] 4,056,333

[45] Nov. 1, 1977

[54] INTRAVENOUS FEEDING PUMP FAILURE ALARM SYSTEM

[75] Inventor: Ingemar H. Lundquist, Oakland, Calif.

[73] Assignee: Valleylab, Boulder, Colo.

[21] Appl. No.: 635,656

[22] Filed: Nov. 26, 1975

Related U.S. Application Data

[63] Continuation of Ser. No. 488,581, July 15, 1974, abandoned.

[51] Int. Cl.$^2$ .............. F04B 21/00; A61M 5/16; F04B 49/10
[52] U.S. Cl. ................. 417/44; 128/214 C; 128/DIG. 13; 417/9; 417/43; 417/48; 417/63
[58] Field of Search .............. 417/40, 43, 44, 9, 63, 417/38, 211.5; 200/83; 128/214 E, 214 C, 214 F, 218 A, DIG. 12, DIG. 13, DIG. 1, 1 D

[56] References Cited

U.S. PATENT DOCUMENTS

| | | | |
|---|---|---|---|
| 1,853,811 | 4/1932 | Hewitt | 417/9 |
| 2,672,051 | 3/1954 | Butler | 128/214 C |
| 2,767,277 | 10/1956 | Wirth | 417/43 |
| 2,880,909 | 4/1959 | Clymer et al. | 200/83 J |
| 2,907,325 | 10/1959 | Burke | 128/214 C |
| 3,543,752 | 12/1970 | Hesse | 128/214 E |
| 3,559,644 | 2/1971 | Stoft | 128/214 F |
| 3,874,826 | 4/1975 | Lundquist | 128/214 F |
| 3,884,228 | 5/1975 | Hahn | 128/214 F |
| 3,901,231 | 8/1975 | Olson | 128/214 F |

*Primary Examiner*—Willliam L. Freeh
*Attorney, Agent, or Firm*—Flehr, Hohbach, Test, Albritton & Herbert

[57] ABSTRACT

The present invention relates to a failure alarm system for an intravenous feeding pump in which the pumping force is secured by the projection of a plunger into a chamber filled with the liquid to be pumped, which plunger is encased in a tightly fitting sheath of elastic material. In such a pump, actuation is secured by the application of a force from an actuator to the end of the plunger extending without the wall of a pumping chamber and the return force is secured by the elasticity of the sheath. The actuator of such a pump provides an actuator which can be selectively set to provide an extended range of operations per unit of time and can be modified to control the amount of projection into the pumping chamber by the plunger. In such a combination means is provided by the present invention for sensing the fact that there is a negative pressure, or suction, in the system that is not balanced by the in-flow of liquid, i.e., the amount of fluid delivered to the pump for each operation is less than that required by the setting (thus sensing when a supply is shut off, or less than the preset amount of liquid is reaching the pump).

14 Claims, 4 Drawing Figures

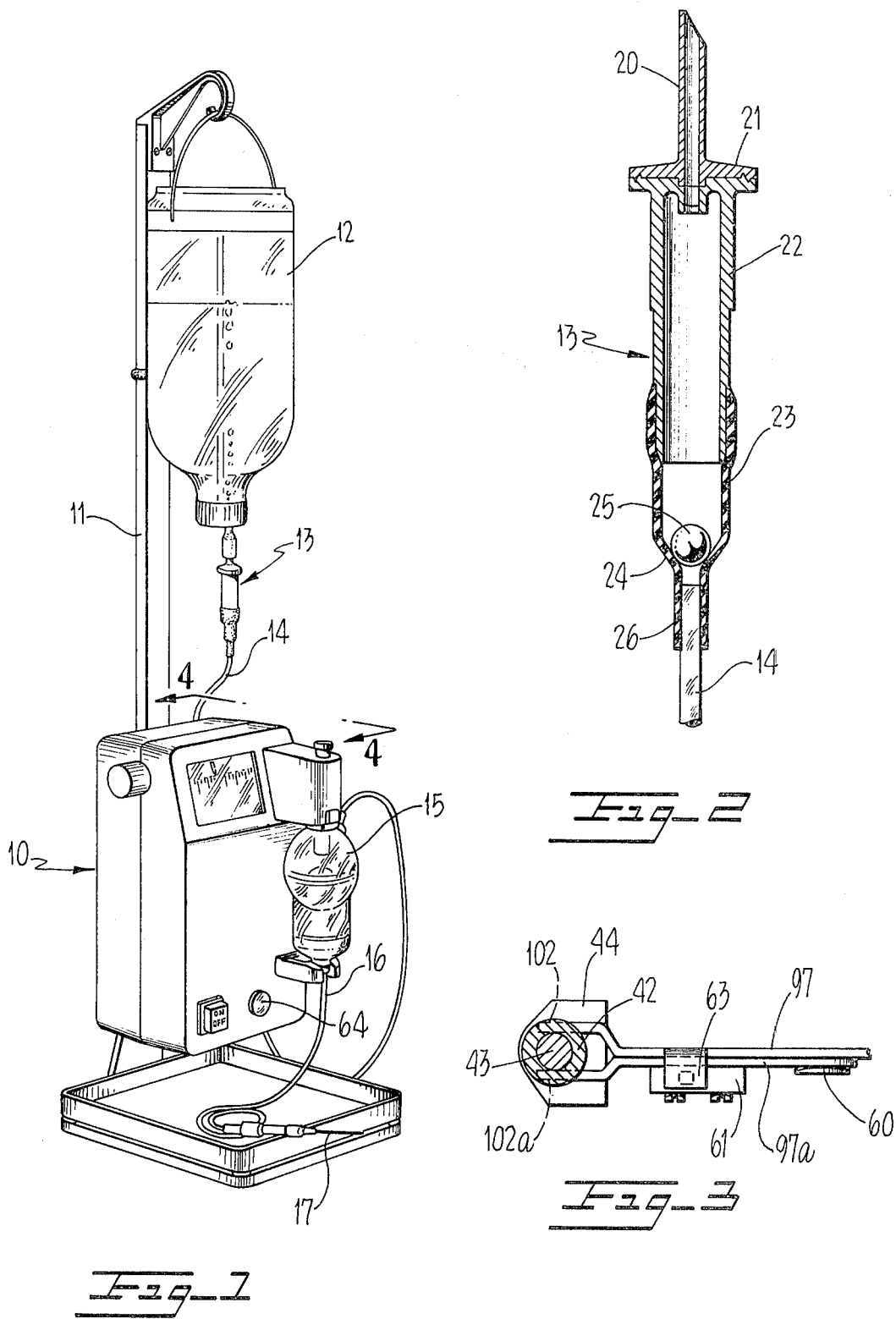

INTRAVENOUS FEEDING PUMP FAILURE ALARM SYSTEM

This is a continuation of application Ser. No. 488,581 filed July 15, 1974 now abandoned.

BACKGROUND OF THE INVENTION

In recent years there has been considerable interest in intravenous delivery pumps, particularly for the feeding of saline solutions, whole blood, or the like, to a patient. For many years such materials were fed to a patient only by the force of gravity which necessitated the placing of a container containing the liquid for delivery to a patient at a considerable elevation above the patient. Such a procedure involves frequent checking by a competent person to see that the apparatus was actually feeding the material at the desired rate, as due to the small amount introduced per minute there was frequent clogging of the delivery tube or needle which is used to deliver the material into the vein of the patient. Regulation of flow could only be secured by counting drops of fluid in a predetermined period of time and then figuring the amount delivered per minute. It was found that it was difficult to maintain a regulated flow over a prolonged period of time. Within the past few years, several efforts have been made to provide an accurate pump which would positively deliver the feeding solution to the patient. This necessitates a pump system of extreme accuracy as well as one which will be completely sterile at all times. Such pumps have the advantage that they do not require the placing of the bottle of material to be fed to the patient at a considerable distance above him. They should be very accurate in their delivery and should be readily adjusted. The difficulties with pumps in the past have been, for the most part, too, that they were subject to slight variations in the quantity of material delivered, so that absolute accuracy was still impossible. Also, they are rather expensive to manufacture so that they could not be sold at a price which would permit them to be used once and then thrown away, and were difficult to disassemble, sterilize and reassemble under sterile conditions. In my application, Ser. No. 431,753, filed Jan. 8, 1974 abandoned in favor of application Ser. No. 556,549 which was abandoned in favor of application Ser. No. 704,540, I propose a pump in which these difficulties have been removed by utilizing a pump in which the pumping chamber was always full of the fluid to be pumped and the pumping force was secured by the projection of a plunger into the body of fluid — the amount of projection being controllable within certain limits and the number of operations per unit of time being also adjustable. In this invention, the plunger was enclosed in a tightly fitting sheath which prevented the entrance of air between the sheath and the plunger, the sheath being sealed to the wall of the pumping chamber so that an air-tight seal or germ barrier was provided between the outside atmosphere and the interior of the pumping chamber.

Associated with such a pump was a driver, such as that disclosed in my patent, U.S. Pat. No. 3,798,982, patented Mar. 26, 1974, in which an arm (97 in said patent) was rocked to depress the plunger and project it into the interior of the pumping chamber. In this patent it was explained how the number of times arm 97 was rocked per unit of time was controlled by the operation of one of a number of cams (51 to 72 in said patent) and the length of each stroke was controlled by the setting of a number of setting members (set screws 111 in said patent). The present invention relates to the combination of the pump of said application, briefly described in said patent, and the actuator of said patent modified as hereinafter described. Such an alarm system is operative when any of three conditions exist: (a) when the supply of material to the pump is shut off or even partially closed, as by the accidental closing of the manual clamp that is normally placed on the outlet tube from the supply container material, the inlet tube is disconnected from the source of supply, and the like; (b) when the supply in the container is exhausted; or (c) when for some reason (such as leakage in the pump, breakage of the sheath enclosing the plunger, or the like) there is less fluid delivered to the pump than specified by the actuator setting. The use of this alarm system permits the operator to exchange bottles of material to be fed to the patient without the admission of any air into the pumping system, so all that is necessary is to remove the conventional hollow needle at the inlet end of the inlet tube from the rubber stopper of the bottle and its immediate insertion into another.

OBJECTS

The primary object of the present invention is to provide an alarm system for an intravenous feeding pump, which system is operated under any condition which prevents the delivery of the set amount of liquid per stroke from the pump and thus includes either the delivery of less than that determined by the setting of the pump actuator or the shut-off of the delivery from the supply vessel to the pump.

It is a further object of the present invention to provide an alarm system for an intravenous pump in which suction is applied to the pumping chamber to secure the replacement of material pumped therefrom whenever anything happens to prevent the suction effect from bringing liquid into the pumping chamber.

Another object of the present invention is to provide an alarm unit which is effective to sense any failure of suction in the pumping chamber to bring in an amount of fluid to fill the chamber These and other objects of the present invention will be apparent from the detailed specification which follows when taken in view of the drawings which are a part hereof.

DRAWINGS

FIG. 1 is a perspective view of a pump of the type mentioned and its actuator as modified by the present invention.

FIG. 2 is an enlarged detail of the drip chamber, i.e., the hollow needle and related devices used to connect the pump and its supply tube to the container containing the fluid to be pumped.

FIG. 3 shows a plan view of the operating arm and the associated sensing member of the present invention, such as a view taken along the planes indicated by the lines 3—3 of FIG. 4.

Figure 4:
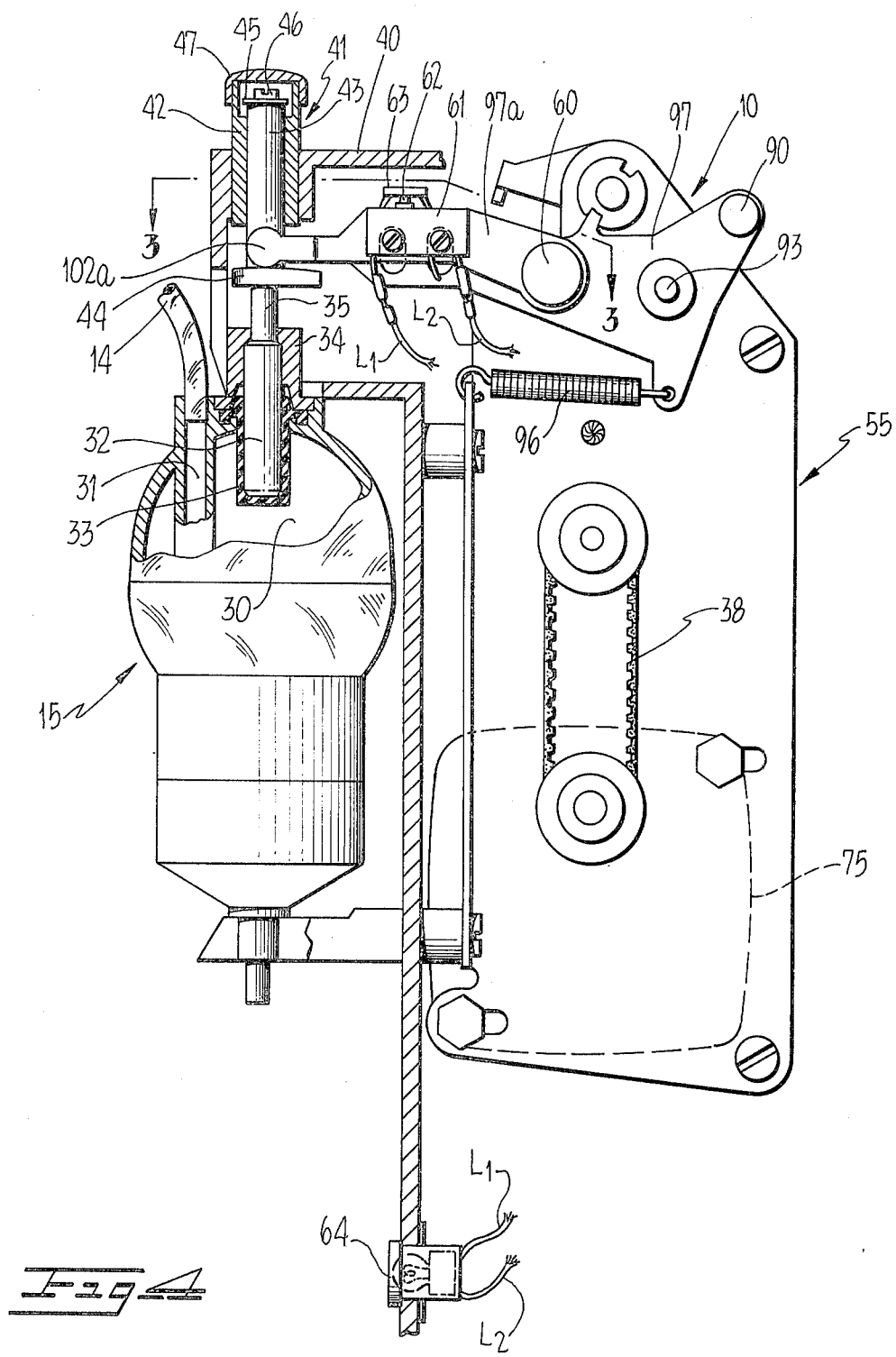
FIG. 4 is a side view, partly in cross-section, showing particularly the pump actuating arm and the sensing devices associated therewith in position to drive a pump of the type mentioned.

As best shown in FIG. 1, the pump actuator 10 of the present invention preferably is adapted to be mounted on a suitable stand 11. The stand will be provided with a suitable holder for a bottle 12 to be used for intravenous feeding. Material from the bottle with first flow into a bubble trap, or drip chamber, 13 and thence into a delivery tube 14 to a pump 15 and thence through a tube 16 to a needle 17 to be inserted in the arm of a patient. The bubble trap 13 of the present invention is modified from that which is conventional in this type of equipment, as shown in FIG. 2. It comprises a hollow needle 20 adapted to be inserted through the rubber stopper of the bottle 12 of material to be fed to the patient. This needle is provided with an enlarged shoulder 21, as shown in FIG. 2, to limit the depth of insertion into the bottle 12. The needle and its shoulder 21 connect with an upper section 22 of the bubble trap, as shown. The needle 20 and upper section of the bubble trap, or drip chamber, 22 are formed of a rigid material, so that the needle can be inserted through the rubber stopper and neither are readily deformable, either from atmospheric pressure or manual manipulation by an operator. The lower end of the bubble trap is enclosed within a tightly fitting tube 23 of very soft and resilient material which is readily deformable by manipulation. The lower end of this tube, or sheath, has a sloping conical section 24 leading from the enlarged diameter of the upper section 23 and the lower end 26 which is adapted to receive the delivery tube 14 leading to the pump. A relatively soft ball 25 is enclosed within the soft lower section 23 of the sheath, which ball will float in a liquid to be fed to a patient and which is somewhat larger than the lower section 26 which receives the delivery tube 14. In many devices of this kind, the delivery tube has an inner diameter of about ⅛ inch, in which case the ball 25 would have a diameter of about ¼ inch and the flexible sheath would have a diameter of about ½ inch.

The pump 15 comprises a pumping chamber 30 (see FIG. 4) with an inlet 31 adapted to receive the delivery tube 14 and a suitable valve for closing the inlet, not shown, but which is readily understood by those skilled in the art, and which may take various forms, one of which is included in the specification of the copending application above-mentioned. The pumping displacement force is secured by the actuation of a plunger 32 which extends through the wall of the chamber 30, a portion of said plunger lying inside chamber, and a portion lying to the outside thereof as shown in FIG. 4. The inner end of the plunger 32 is enclosed in a tightly embracing sheath 33, the outer end of which is sealed to the wall of the pumping chamber 30, as by a cap 34 which encloses a major portion of the outer end of the plunger 32. At the extreme outer end of the plunger 32 is a smaller stem 35 which extends through an opening in the cap 34. Thus, the cap serves to retain the plunger in operating position but permits the stem 34 to extend outside thereof so as to be subject to operation by the actuator hereinafter mentioned.

The sheath 33 is formed of an elastic material, such as rubber, with an elastic force sufficient to retract the plunger 32 after it has been projected by the actuator into the pumping chamber from the position shown in FIG. 4, and will operate with sufficient force also to provide a suction within the chamber 30 sufficient to operate the normally closed inlet valve, not shown, to draw fluid to be pumped into the chamber 30. It will be understood that in operation, the pump chamber 30 is completely filled with liquid whereby the projection of the plunger 32 and its sheath 33 into the chamber will displace an amount of fluid determined in direct proportion to the amount of projection of the plunger into the chamber. At the end of a stroke, an outlet valve, not shown, but well understood by those skilled in the art, will close to prevent the back-flow of pump fluid back into the pumping chamber 30. Upon release of the actuating force through the arm 95 of the actuator, elasticity of the rubber sheath 33 will force the plunger outwardly to the limit of cap 34, thereby creating suction within the pump chamber 30 to draw more fluid thereinto.

Aligned with the plunger 32 and mounted in the casing 40 of the actuator, is a manually operated button 41. In the patent mentioned, this button was a solid member. In the present invention the button 41 comprises an outer cylindrical section 42; an inner core 43, at the inner end of which is a shoulder, or buttress, 44, the lower face of which abuts the stem 35 of the plunger and the upper face of which engages the circular tip 102a of the operating arm 97 (FIG. 4). The core 43, while embraced within the cylindrical section 42 of the button 41, is freely slidable therein. It is retained within the interior of the cylinder 42 by means of a washer 45 and screw 46. As shown in FIG. 4, there is some play between the inner core 43 and the outer section 42, so that the outer section can be raised when arm 97 is raised without lifting the inner core 43. A cap 47 fastened to the outer section 42 completes the button assembly.

The rocking of the operating arm 97 is described in complete detail in the patent above-mentioned and it is therefore believed unnecessary to be repeated here. Suffice to say that the arm is rocked through a pin 90 mounted on an arm (88 in said patent) under the control of a selected one of a number of cams in the actuator. The arm 97 is privotally mounted on a stud 93 and is resiliently returned to an inoperative position (which is shown in FIG. 4) by a spring 96. When rocked by the actuator counterclockwise from the position shown in FIG. 4, the circular tip 102 of the arm 97 operating upon the flange, or shoulder, 44, depresses the plunger 32 into the interior of the pumping chamber 30. When the driving member is released by its cam, the spring 96 quickly rocks the arm 97 back to the inoperative position. Thereupon the circular tip 102 of the operating arm 97 (similar in shape to 102a shown in FIG. 4 and shown as 102 in FIG. 3 of the patent above-mentioned) will lift the outer cylinder 42 of the button 41. Since the core 43 is readily slidable within the cylindrical section 42, the core 43 and shoulder 44 will not be lifted by the return of arm 97 to its inoperative position but is raised by the force of the plunger 32 resulting from the elasticity of the sheath 33, if the suction created by such movement is sufficient to bring additional fluid into the pumping chamber 30. However, if, for any reason the supply of fluid to the pumping chamber 30 was shut off, as by an exhaustion of the supply of fluid from the container 12, or some other cause restricting the inflow of material into the pump, the suction so caused will prevent the raising of the plunger 32, for the elasticity of the sheath is insufficient to overcome both the force of gravity caused by the weight of the plunger and the force of the suction so created. It is obvious that so long as fluid flows from the supply container 12, the ball 25 will float within the bubble chamber 13 and fluid will be permitted to flow into the inlet tube 14. However, when that supply is exhausted, the ball 25 will settle to the bottom and will effectively seal the entrance to tube 14 before the liquid level will reach the line at which the ball seals the conical section 24 of the bubble chamber. It will be understood that the ball 25, while sufficiently light to float in liquid, is sufficiently heavy that only a minor portion of the ball will be above fluid level. Once the ball 25 seats on the conical section 24, a perfect seal is formed and thereafter no material can flow into the inlet tube 14 and hence there will be a vacuum in pumping chamber 30 which will prevent the return of the plunger 32 to its inoperative position.

While a number of means for sensing this situation could be suggested, one of the most simple is shown in FIGS. 3 and 4. The preferred embodiment of the sensing device comprises a secondary arm 97a which is rotatably mounted on the actuator drive arm 97 by any suitable means, such as pivot stud 60. It will be understood that the arm 97a rocks freely on the arm 97. The arm 97a is provided with a circular tip 102a which rests upon the flange 44 on the opposite side of the core member 43 from the tip (102 in the patent) on the arm 97 and underlies the outer casing 42 of the button 41. The arm 97a carries a switch 61 having a control button 62. A flange 63 integral with the arm 97 overlies the button 62 and normally will depress it. A pair of leads L-1 and L-2 lead to the switch 61. It will be understood that if the alarm system is to cause the lighting of a signal light, such as 64 (FIG. 4), or the sounding of a buzzer or gong, switch 61 will normally be open and will be closed to provide a circuit to the alarm element by the separation of the flange 63 on arm 97 from the button 62 on the switch 61. On the other hand, if it is desired that the sensing of the condition above-mentioned is to stop operation of the pump, such as by shutting off the motor 75 which drives the actuator mechanism, the switch 61 would normally be closed and the separation of the flange 63 from the button 62 would be operative to open that circuit and thereby stop the motor. Another alternative will do both, that is, stop the motor 75 and energize an alarm, such as the light 64, in which case the switch 61 would be of the double-throw type in which one circuit would be normally open and the other normally closed and the separation of the flange 63 from the button 62 would reverse the setting. Such alternatives will be obvious to those skilled in the art. At this point it can be mentioned that the switch 61 will control the flow of power to an alarm element, such as the light 64, through suitable leads connecting the two, or in the alternative to the motor 75.

The operation of the device is believed obvious to those skilled in the art, but perhaps should be briefly stated. The actuator 55, when operating, will cause the rocking of the arm 97 through an arc, the length of which is controlled by suitable mechanism within the actuator as described in said patent, and at timed intervals, again depending upon the setting of the actuator as described in my aforesaid patent. Rocking of the arm 97 (counter-clockwise when viewed in FIG. 4) will depress the plunger 32 of the pump through the medium of the flange 44 on the core 43 of the button 41. When normal operating conditions exist, the return of the arm 97 (clockwise in FIG. 4) release the pressure on the plunger 32 whereupon the elasticity of the sheath 33 will cause the plunger 32 to move to the retracted position as fast as the arm 97 is lifted. In this case, the suction created by the withdrawal of the plunger 32 will draw into the pumping chamber 30 an amount of fluid equal to that which has just been dicharged. So long as this condition exists, the arm 97a will move in both directions simultaneously with the arm 97, since the flange 63 overlying the switch 61 will depress the arm 97a and the rise of the plunger 32 will lift the flange 44 and core 43 of the manual button 41, thereby keeping the button 62 of the switch in engagement with the flange 63. In this condition, operation of the pump is continuous. However, if some condition exists which prevents the return of the plunger 32 to its retracted position as fast as the arm 97 is rocked back to its inoperative position, the arm 97a will continue to ride on flange 44 of the core 43 of the control button 41, whereupon the flange 63 on operating arm 97, is lifted from engagement with the button 62 of the switch, thereby causing the opening or closing of the switch, as the case may be. This situation will develop in the event the supply of fluid 12 is exhausted as in that event the ball 65 of the bubble trap 13 will from a sealing engagement with the conical section 24 of the soft and very flexible section of the bubble trap. This creates a suction, or negative pressure, within the supply tube 14 and pump chamber 30 which counteracts the elasticity of the sheath 63 — and the plunger 32 is therefore unable to rise. The situation would also occur if the manual clamp usually used in connection with a feed tube 14 is shut off deliberately or accidentally, as the same situation would exist as if the supply in bottle 12 were exhausted. The situation would also exist in the event of some breakage or misoperation of the sheath 33, as that would cease to provide the elastic force necessary to return the plunger to its inoperative position. In any of these events, the signal, which may be a light 64, will be operated, or if the other type of control is used, the pump actuator will cease to operate. In such a situation, if the return of the plunger 32 were slower than the return of arm 97, there would be a flickering of the alarm system unless a holding relay were provided in the alarm circuit.

It should perhaps be explained that in the event the float 25 becomes seated on the conical section 24 of the highly flexible section 23, no air can enter the tube 14 and hence cannot enter the pumping chamber 30. The air trap 13 can then be removed from the bottle 12 without danger of air entering the pump. When the needle 20 is inserted through the plug of a new bottle of material, there will, of course, be some air trapped in the upper portion of the bubble trap. Since the section 23 is highly resilient, or soft, a little pressure by an operator on the cylindrical section above the sealing ball 24 will start the flow of liquid — the air in the bubble trap flowing through the needle into the bottle. This permits the escape of whatever air has entered the bubble trap 22 upwardly through the needle 20 into the upper portion of the bottle 12. After the bubble trap has a sufficient amount of liquid, pressure on the resilient conical section 24 below the ball 25 will lift the ball 25 out of its sealing position and liquid can flow through the needle delivery tube 14 without the entrapment of any air therein. Hence, no air will be delivered to the pumping chamber 30 and if it were, the air would rise in the pumping chamber and effect the operation of the plunger 32. It is an inherent characteristic of pumps of the type herein mentioned that the entrapment of air in the pump chamber 30 will affect the operation of the pump since the air is readily compressible while the liquid is not. In that event, the pump operation will compress the air which will expand when the actuating arm 97 returns to its inoperative position, and if enough air is permitted to enter the pumping chamber 30, the pump will cease to deliver any material at all. This situation is immediately obvious to an observer and indicates that the pump has been carelessly operated and should be corrected immediately.

It will be understood that in place of a light 64, a jack could be provided into which could be inserted the end of a signal circuit which leads from the bed of the patient to the nurse's station of a hospital, and many hospitals are now being equipped with such signal devices.

It will also be understood that this invention is applicable to any pump in which the plunger 32, or a piston in a piston pump, is returned to its inoperative position by any resilient biasing force, such as a spring.

It is obvious that many slight modifications can be made in the preferred form of the present invention, such as the type of alarm to be used and the like. Accordingly, the claims should be given an interpretation commensurate with the wording.

What is claimed is:

1. In combination with an intravenous feeding pump having:
   a. pumping chamber having an inlet and an outlet,
   b. inlet valve means disposed in the inlet and outlet valve means disposed in the outlet,
   c. a plunger serving as a pumping member projecting through the wall of said chamber and having an outer end portion always extending out of said chamber whereby the plunger can be reciprocated between first and second positions in said chamber,
   d. resilient biasing means for returning said plunger to the first position,
   e. a pump actuator having means adapted to urge the outer end of said plunger to the second position against the force of the resilient biasing means and; an alarm system comprising:
      1. means for sensing failure of said plunger to return to its inoperative position, and
      2. signal means operated by said sensing means.

2. The apparatus of claim 1 wherein the signal means comprises:
   (a) a sensing arm movable to one position by said actuator as the actuator moves the plunger to said second position and movable to another position by the force of said resilient biasing means;
   (b) a switch held in one position by conjoint movement of the sensing arm and the actuator means and movable to another position when said sensing arm and said actuator means move independently of each other and wherein the signal means operated by movement of said switch to said another position.

3. In combination with an intravenous feeding pump having:
   a. a pumping chamber,
   b. an inlet into and an outlet from said pumping chamber and an inlet valve disposed in the inlet and an outlet disposed in the outlet,
   c. a plunger serving as a pumping member projecting through the wall of said chamber whereby the plunger can be pushed inwardly into said chamber, and
   d. an elastic sheath tightly enclosing the interior section of said plunger, which sheath is sealed to the wall of said chamber to provide an air-tight seal therewith, and
   e. a pump actuator having a rocking arm effective to depress the outer end of said plunger; an alarm system comprising:
      1. means for sealing the inlet to said pumping chamber upon termination of fluid flow into said inlet,
      2. a sensing arm rocked to one position by said actuator arm as the latter moves to project the plunger into said pumping chamber but returned to the other position only by the force of the elastic sheath,
      3. a switch held in one position by the conjoint movement of the auxiliary arm and the rocking arm but set to the other position by the separation of the rocking arm and the sensing arm, and
      4. signal means operated by the change in the condition of said switch.

4. The apparatus of claim 3 wherein the inlet to said pumping chamber is provided with a very soft and resilient tubular section and a float in said section adapted to seal said inlet in the event the supply of fluid to be pumped is exhausted.

5. The apparatus of claim 3 wherein the switch is mounted upon one of said arms, and the other of said arms carries a member adapted to bear upon said switch.

6. The apparatus of claim 3 wherein the sensing arm is rotatably mounted on said rocking arm.

7. In an intravenous fluid delivery system for use with a container of I.V. fluid, means forming a drip chamber, said drip chamber having a wall with at least a portion of the same which is transparent, said means forming a drip chamber including a resilient lower member having an outlet formed therein, means carried by the drip chamber adapted to form a connection to said container whereby I.V. fluid can pass from the container into the drip chamber, a ball-like member disposed within said drip chamber and being capable of floating in said I.V. fluid, said ball-like member being of a size so it is capable of closing said outlet when drip chamber is empty of I.V. fluid and is disposed in a vertical direction with the outlet extending downwardly, means forming a pump chamber having an inlet and an outlet, inlet valve means disposed in the inlet, outlet valve means disposed in the outlet, means for connecting the outlet of the drip chamber to the inlet of the pump chamber, means connecting the outlet to a patient, a plunger serving as a pumping member, means for causing reciprocatory movement of said plunger for causing movement of I.V. fluid through said pump chamber from said inlet to said outlet of said pump chamber and means for sensing when the reciprocatory movement of said plunger ceases and for giving an alarm.

8. A system as in claim 7 together with lever arm means for moving said plunger in at least one direction.

9. Apparatus as in claim 8 together with resilient means for moving said plunger in a direction opposite said one direction.

10. A system as in claim 9 wherein said means for moving said plunger in the opposite direction is of insufficient strength to move said plunger in said opposite direction when greater than a predetermined vacuum occurs in said pumping chamber.

11. In an alarm apparatus for use with an intravenous fluid delivery system including a pump having a pumping chamber and an inlet and an oulet in communication with the pumping chamber, inlet valve means disposed in the inlet, outlet valve means disposed in the outlet, a plunger serving as a pumping member, means for causing reciprocatory movement of said plunger to cause movement of intravenous fluid through said pumping chamber from the inlet through said outlet and means for sensing when the reciprocatory movement of said plunger ceases and for giving an alarm when such a condition is sensed, said means for causing reciprocatory movement including lever arm means for moving said plunger in at least one direction, said means for sensing the reciprocatory movement of said plunger including means for sensing the movement of said lever arm, resilient means for moving said plunger in the opposite direction, said resilient means being of insufficient strength to return said plunger in the opposite direction when a vacuum condition is created in said pumping chamber in excess of a predetermined value.

12. In an alarm apparatus for use with an intravenous fluid delivery system including a pump having a pumping chamber and an inlet and an outlet in communication with the pumping chamber, inlet valve means disposed in the inlet, outlet valve means disposed in the outlet, a drip chamber in communication with the inlet of the pumping chamber, said drip chamber having a wall with at least a portion of the same being transparent, said means forming a drip chamber including a resilient lower member having an outler formed therein, a ball-like member disposed in the chamber and being capable of floating in the intravenous fluid, said ball-like member being capable of closing said oulet in said drip chamber when said drip chamber is empty of intravenous fluid and is vertically disposed with the outlet extending downwardly, a plunger serving as a pumping member, means for causing reciprocatory movement of said plunger to cause movement of intravenous fluid through said pumping chamber from the inlet through said outlet and means for sensing when the reciprocating movement of said plunger ceases and for giving an alarm when such a condition is sensed.

13. Apparatus as in claim 12 wherein said resilient lower member is of sufficient length so that it can be manually manipulated.

14. In a method for initiating an alarm for use with an intravenous liquid delivery system including a pump and a drip chamber having an inlet and an oulet in which the lower portion of the drip chamber is defined by a deformable member having an oulet therein and in which a ball capable of floating in the liquid is provided in the drip chamber, connecting the drip chamber to a source of intravenous liquid, repeatedly squeezing the deformable member defining the drip chamber to cause intravenous liquid to enter into the drip chamber and to at least partially fill the drip chamber so that the ball floats in the liquid in the drip chamber and permits the liquid to flow through the outlet to the pump, supplying intravenous liquid to the patient by the use of the pump, creating a vacuum condition in the pump when all of the liquid has been dispensed from the drip chamber by permitting the ball to close off the oulet in the drip chamber and initiating an alarm in response to creating of the vacuum condition.

* * * * *